US012295843B2

(12) United States Patent
Glazier et al.

(10) Patent No.: US 12,295,843 B2
(45) Date of Patent: *May 13, 2025

(54) SYSTEM TO ASSIST IN THE RELEASE OF A COLLAPSIBLE STENT FROM A DELIVERY DEVICE

(71) Applicant: St. Jude Medical, Cardiology Division, Inc., St. Paul, MN (US)

(72) Inventors: Valerie J. Glazier, Eden Prairie, MN (US); Ralph Joseph Thomas, Champlin, MN (US); Khoi Le, Excelsior, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 141 days.

This patent is subject to a terminal disclaimer.

(21) Appl. No.: 18/173,422

(22) Filed: Feb. 23, 2023

(65) Prior Publication Data
US 2023/0200992 A1  Jun. 29, 2023

Related U.S. Application Data

(60) Continuation of application No. 17/242,716, filed on Apr. 28, 2021, now Pat. No. 11,612,483, which is a
(Continued)

(51) Int. Cl.
*A61F 2/24* (2006.01)

(52) U.S. Cl.
CPC .......... *A61F 2/2436* (2013.01); *A61F 2/2418* (2013.01); *A61F 2/243* (2013.01);
(Continued)

(58) Field of Classification Search
CPC ...... A61F 2/2436; A61F 2/2418; A61F 2/243; A61F 2/2433; A61F 2230/0013; A61F 2230/008
See application file for complete search history.

(56) References Cited

U.S. PATENT DOCUMENTS

| 4,423,730 A | 1/1984 | Gabbay |
| 4,471,777 A | 9/1984 | McCorkle, Jr. |

(Continued)

FOREIGN PATENT DOCUMENTS

| DE | 102004062296 A1 | 7/2006 |
| EP | 1129744 A1 | 9/2001 |

(Continued)

OTHER PUBLICATIONS

International Search Report and Written Opinion for Application No. PCT/US2011/001218 dated Nov. 11, 2011.
(Continued)

*Primary Examiner* — Alexander J Orkin
(74) *Attorney, Agent, or Firm* — SLEMAN & LUND LLP (57) ABSTRACT

A delivery device for an implantable medical device having a retention member at an end thereof may include a shaft extending in a longitudinal direction and defining a longitudinal axis, an elongated sheath surrounding a longitudinal portion of the shaft, a compartment defined inside the sheath and adapted to receive the medical device in an assembled condition, a retainer positioned at one end of the compartment, and an energy storage element positioned on the longitudinal portion of the shaft and configured to be radially compressed by the medical device when the elongated sheath covers the compartment containing the medical device. The sheath may be slidable relative to the shaft in the longitudinal direction. The retainer may include a recess adapted to receive the retention member of the medical device in the assembled condition.

12 Claims, 5 Drawing Sheets

Related U.S. Application Data division of application No. 15/921,050, filed on Mar. 14, 2018, now Pat. No. 11,026,789, which is a division of application No. 13/790,819, filed on Mar. 8, 2013, now Pat. No. 9,918,837.

(60) Provisional application No. 61/666,209, filed on Jun. 29, 2012.

(52) U.S. Cl.
CPC ..... *A61F 2/2433* (2013.01); *A61F 2230/0013* (2013.01); *A61F 2230/008* (2013.01)

(56) References Cited

U.S. PATENT DOCUMENTS

| | | | |
|---|---|---|---|
| 4,546,759 A | 10/1985 | Solar | |
| 4,575,371 A | 3/1986 | Nordqvist | |
| 5,090,958 A | 2/1992 | Sahota | |
| 5,120,299 A | 6/1992 | Lombardi | |
| 5,201,901 A | 4/1993 | Harada | |
| 5,334,160 A | 8/1994 | Ellis | |
| 5,411,552 A | 5/1995 | Andersen | |
| 5,733,325 A | 3/1998 | Robinson | |
| 5,766,151 A | 6/1998 | Valley | |
| 5,795,325 A | 8/1998 | Valley | |
| 5,797,952 A | 8/1998 | Klein | |
| 5,827,324 A | 10/1998 | Cassell | |
| 5,868,706 A | 2/1999 | Cox | |
| 5,868,755 A | 2/1999 | Kanner | |
| 5,924,424 A | 7/1999 | Stevens | |
| 5,968,068 A | 10/1999 | Dehdashtian | |
| 5,980,533 A | 11/1999 | Holman | |
| 6,051,014 A | 4/2000 | Jang | |
| 6,077,295 A | 6/2000 | Limon | |
| 6,139,517 A | 10/2000 | Macoviak | |
| 6,146,415 A | 11/2000 | Fitz | |
| 6,190,357 B1 | 2/2001 | Ferrari | |
| 6,214,036 B1 | 4/2001 | Letendre | |
| 6,231,588 B1 | 5/2001 | Zadno-Azizi | |
| 6,306,141 B1 | 10/2001 | Jervis | |
| 6,312,407 B1 | 11/2001 | Zadno-Azizi | |
| 6,361,545 B1 | 3/2002 | Macoviak | |
| 6,375,668 B1 | 4/2002 | Gifford | |
| 6,482,228 B1 | 11/2002 | Norred | |
| 6,592,612 B1 | 7/2003 | Samson | |
| 6,607,551 B1 | 8/2003 | Sullivan | |
| 6,623,518 B2 | 9/2003 | Thompson | |
| 6,673,040 B1 | 1/2004 | Samson | |
| 6,776,791 B1 | 8/2004 | Stallings | |
| 7,235,095 B2 | 6/2007 | Haverkost | |
| 8,414,644 B2 | 4/2013 | Quadri | |
| 8,608,792 B2 | 12/2013 | Silveira | |
| 8,641,749 B2 | 2/2014 | Barthold | |
| 11,612,483 B2 * | 3/2023 | Glazier | A61F 2/243 623/2.11 |
| 2002/0099435 A1 | 7/2002 | Stinson | |
| 2002/0120323 A1 | 8/2002 | Thompson | |
| 2003/0014007 A1 | 1/2003 | Eidenschink | |
| 2003/0023265 A1 | 1/2003 | Forber | |
| 2003/0050694 A1 | 3/2003 | Yang | |
| 2003/0199963 A1 | 10/2003 | Tower | |
| 2004/0087900 A1 | 5/2004 | Thompson | |
| 2004/0093063 A1 | 5/2004 | Wright | |
| 2004/0204749 A1 | 10/2004 | Gunderson | |
| 2004/0236406 A1 | 11/2004 | Gregorich | |
| 2004/0267346 A1 | 12/2004 | Shelso | |
| 2004/0267348 A1 | 12/2004 | Gunderson | |
| 2005/0020974 A1 | 1/2005 | Noriega | |
| 2005/0027345 A1 | 2/2005 | Horan | |
| 2005/0033398 A1 | 2/2005 | Seguin | |
| 2005/0049667 A1 | 3/2005 | Arbefeuille | |
| 2005/0049674 A1 | 3/2005 | Berra | |
| 2005/0065590 A1 | 3/2005 | Shelso | |
| 2005/0090890 A1 | 4/2005 | Wu | |
| 2005/0222662 A1 | 10/2005 | Thompson | |
| 2006/0058865 A1 | 3/2006 | Case | |
| 2006/0100688 A1 | 5/2006 | Jordan | |
| 2006/0106415 A1 | 5/2006 | Gabbay | |
| 2006/0111771 A1 | 5/2006 | Ton | |
| 2006/0142848 A1 | 6/2006 | Gabbay | |
| 2006/0149294 A1 | 7/2006 | Argentine | |
| 2006/0167468 A1 | 7/2006 | Gabbay | |
| 2006/0195184 A1 | 8/2006 | Lane | |
| 2006/0229698 A1 | 10/2006 | Larson | |
| 2006/0259120 A1 | 11/2006 | Vongphakdy | |
| 2006/0276872 A1 | 12/2006 | Arbefeuille | |
| 2007/0027534 A1 | 2/2007 | Bergheim | |
| 2007/0073391 A1 | 3/2007 | Bourang | |
| 2007/0088431 A1 | 4/2007 | Bourang | |
| 2007/0106364 A1 | 5/2007 | Buzzard | |
| 2007/0112422 A1 | 5/2007 | Dehdashtian | |
| 2007/0129749 A1 | 6/2007 | Thomas | |
| 2007/0142858 A1 | 6/2007 | Bates | |
| 2007/0162100 A1 | 7/2007 | Gabbay | |
| 2007/0168013 A1 | 7/2007 | Douglas | |
| 2007/0203561 A1 | 8/2007 | Forster | |
| 2007/0203575 A1 | 8/2007 | Forster | |
| 2007/0233224 A1 | 10/2007 | Leynov | |
| 2007/0239271 A1 | 10/2007 | Nguyen | |
| 2007/0293930 A1 | 12/2007 | Wang | |
| 2007/0293942 A1 | 12/2007 | Mirzaee | |
| 2008/0103443 A1 | 5/2008 | Kabrick | |
| 2008/0114442 A1 | 5/2008 | Mitchell | |
| 2008/0114443 A1 | 5/2008 | Mitchell | |
| 2008/0140189 A1 | 6/2008 | Nguyen | |
| 2008/0147182 A1 | 6/2008 | Righini | |
| 2008/0221666 A1 | 9/2008 | Licata | |
| 2008/0228255 A1 | 9/2008 | Rust | |
| 2008/0255662 A1 | 10/2008 | Stacchino | |
| 2008/0262590 A1 | 10/2008 | Murray | |
| 2008/0319526 A1 | 12/2008 | Hill | |
| 2009/0054975 A1 | 2/2009 | Del Nido | |
| 2009/0143851 A1 | 6/2009 | Paul, Jr. | |
| 2009/0204197 A1 | 8/2009 | Dorn | |
| 2009/0222035 A1 | 9/2009 | Schneiderman | |
| 2009/0228093 A1 | 9/2009 | Taylor | |
| 2009/0240320 A1 | 9/2009 | Tuval | |
| 2009/0259306 A1 | 10/2009 | Rowe | |
| 2009/0276027 A1 | 11/2009 | Glynn | |
| 2009/0281610 A1 | 11/2009 | Parker | |
| 2009/0287290 A1 | 11/2009 | Macaulay | |
| 2010/0070015 A1 | 3/2010 | Schneider | |
| 2010/0131039 A1 | 5/2010 | Chau | |
| 2010/0145438 A1 | 6/2010 | Barone | |
| 2010/0152834 A1 | 6/2010 | Hannes | |
| 2010/0268315 A1 | 10/2010 | Glynn | |
| 2010/0274187 A1 | 10/2010 | Argentine | |
| 2010/0312325 A1 | 12/2010 | Dorn | |
| 2011/0029065 A1 | 2/2011 | Wood | |
| 2011/0077731 A1 | 3/2011 | Lee | |
| 2011/0078350 A1 | 3/2011 | Carls | |
| 2011/0098805 A1 | 4/2011 | Dwork | |
| 2011/0137401 A1 | 6/2011 | Dorn | |
| 2011/0137402 A1 | 6/2011 | Dorn | |
| 2011/0172764 A1 | 7/2011 | Badhwar | |
| 2011/0224678 A1 | 9/2011 | Gabbay | |
| 2011/0251665 A1 | 10/2011 | Schmitt | |
| 2011/0251666 A1 | 10/2011 | Schmitt | |
| 2011/0251679 A1 | 10/2011 | Wiemeyer | |
| 2011/0257720 A1 | 10/2011 | Peterson | |
| 2011/0264201 A1 | 10/2011 | Yeung | |
| 2011/0264202 A1 | 10/2011 | Murray, III | |
| 2011/0288636 A1 | 11/2011 | Rolando | |
| 2011/0301685 A1 | 12/2011 | Kao | |
| 2012/0078350 A1 | 3/2012 | Wang | |
| 2012/0123528 A1 | 5/2012 | Knippel | |
| 2012/0179033 A1 | 7/2012 | Merhi | |
| 2013/0116654 A1 | 5/2013 | Dehdashtian | |
| 2013/0131775 A1 | 5/2013 | Hadley | |
| 2013/0204344 A1 | 8/2013 | Tatalovich | |
| 2013/0274860 A1 | 10/2013 | Argentine | |

(56) References Cited

U.S. PATENT DOCUMENTS

| | | |
|---|---|---|
| 2013/0274870 A1 | 10/2013 | Lombardi |
| 2014/0005768 A1 | 1/2014 | Thomas |
| 2014/0031922 A1 | 1/2014 | Duffy |

FOREIGN PATENT DOCUMENTS

| | | | |
|---|---|---|---|
| EP | 1157673 | A2 | 11/2001 |
| WO | 9620025 | A1 | 7/1996 |
| WO | 9748343 | A1 | 12/1997 |
| WO | 9965418 | A1 | 12/1999 |
| WO | 2006069704 | A2 | 7/2006 |
| WO | 2006124549 | A1 | 11/2006 |
| WO | 2007002863 | A2 | 1/2007 |
| WO | 2007134290 | A2 | 11/2007 |
| WO | 2008031103 | A2 | 3/2008 |
| WO | 2008097556 | A1 | 8/2008 |
| WO | 2008138584 | A1 | 11/2008 |
| WO | 2009062955 | A1 | 5/2009 |
| WO | 2009091509 | A1 | 7/2009 |
| WO | 2009108942 | A1 | 9/2009 |
| WO | 2010005524 | A2 | 1/2010 |
| WO | 2010022138 | A2 | 2/2010 |
| WO | 2010051025 | A1 | 5/2010 |
| WO | 2010087975 | A1 | 8/2010 |
| WO | 2011025945 | A1 | 3/2011 |
| WO | 2012009006 | A1 | 1/2012 |
| WO | 2012036740 | A2 | 3/2012 |
| WO | 2012038550 | A1 | 3/2012 |
| WO | 2014004947 | | 1/2014 |

OTHER PUBLICATIONS

International Search Report and Written Opinion for Application No. PCT/US2012/047283 dated Oct. 30, 2012.
International Search Report and Written Opinion for Application No. PCT/US2013/047891 dated Dec. 4, 2013.
International Search Report and Written Opinion for Application No. PCT/US2013/048413 dated Dec. 4, 2013.
International Search Report dated Feb. 2, 2012 for Application No. PCT/US2011/001446.
International Search Report for Application No. PCY/US2011/001596 dated May 8, 2012.

* cited by examiner

SYSTEM TO ASSIST IN THE RELEASE OF A COLLAPSIBLE STENT FROM A DELIVERY DEVICE

CROSS-REFERENCE TO RELATED APPLICATION

This application is a continuation of U.S. patent application Ser. No. 17/242,716, filed Apr. 28, 2021, which is a divisional of U.S. Pat. No. 11,026,789, filed on Mar. 14, 2018, which is a divisional of U.S. Pat. No. 9,918,837, filed Mar. 8, 2013, which claims the benefit of the filing date of U.S. Provisional Patent Application No. 61/666,209, filed on Jun. 29, 2012, the disclosures of which are hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which collapsible valves are mounted: a self-expanding stent and a balloon-expandable stent. To place a collapsible valve into a delivery apparatus and ultimately into a patient, the valve must first be collapsed or crimped to reduce its circumferential size.

When a collapsed valve has reached the desired implant site in the patient (e.g., at or near the annulus of the patient's heart valve that is to be replaced by the prosthetic valve), the prosthetic valve can be released from the delivery apparatus and re-expanded to full operating size.

Despite the various improvements that have been made to the collapsible prosthetic heart valve delivery process, conventional delivery devices, systems, and methods suffer from some shortcomings. For example, the self-expanding collapsible valve may be held in a catheter by stent retention members that are inserted into the retainer portion of the catheter. During deployment of the self-expanding valve into the desired area (e.g., the aortic valve annulus), the delivery process may cause the stent to become twisted relative to the retainer portion of the catheter, which may make it difficult to release the valve because the stent retention members may catch on the retainer during deployment.

There therefore is a need for further improvements to the devices, systems, and methods for transcatheter delivery of collapsible prosthetic heart valves. Among other advantages, the present invention may address one or more of these shortcomings.

BRIEF SUMMARY OF THE INVENTION

Delivery devices for a collapsible prosthetic heart valve and methods of delivering a collapsible prosthetic heart valve using same are aspects of the invention. In addition, any device having one or more of the following features and used in the transcatheter delivery of a collapsible heart valve are specific aspects of the invention.

A delivery device for an implantable medical device having a retention member at an end thereof may include a shaft extending in a longitudinal direction and defining a longitudinal axis, an elongated sheath surrounding a longitudinal portion of the shaft, a compartment defined inside the sheath and adapted to receive the medical device in an assembled condition, a retainer positioned at one end of the compartment, and an energy storage element positioned on the longitudinal portion of the shaft and configured to be radially compressed by the medical device when the elongated sheath covers the compartment containing the medical device. The sheath may be slidable relative to the shaft in the longitudinal direction. The retainer may include a recess adapted to receive the retention member of the medical device in the assembled condition.

The energy storage element may be at least partially aligned with the recess in a circumferential direction about the longitudinal axis. The energy storage element may be an elastomeric element surrounding at least a part of the longitudinal portion of the shaft. A surface of the elastomeric element may have a plurality of raised portions and a plurality of lowered portions distributed in a circumferential direction about the longitudinal axis. The implantable medical device may have a plurality of retention members at the end thereof and the retainer may include a plurality of recesses each adapted to receive a corresponding one of the retention members. Each of the raised portions of the elastomeric element may be at least partially aligned with a corresponding one of the recesses in the circumferential direction.

Each of the lowered portions of the elastomeric element may be disposed between two adjacent ones of the raised portions in the circumferential direction. The elastomeric element may be formed from a material selected from the group consisting of silicone, urethane, nylon, pebax, santoprene, butyl, neoprene, and combinations thereof. The elastomeric element may extend along the shaft in the longitudinal direction throughout the entire length of the compartment. The energy storage element may include a leaf spring attached to the shaft. The leaf spring may extend in a circumferential direction about the longitudinal axis around at least a part of the longitudinal portion of the shaft.

The energy storage element may include a plurality of leaf springs distributed about the shaft in a circumferential direction about the longitudinal axis. Each of the leaf springs may extend in the longitudinal direction along at least a part of the longitudinal portion of the shaft. The energy storage element may be a recess insert, the recess insert overlying a bottom surface of the recess. The recess insert may be a pad of elastomeric material. The recess insert may be a spring.

A method of prosthetic valve delivery may include providing an expandable prosthetic valve having a retention member at an end thereof and loading the valve into a compartment of a delivery device. The delivery device may include a shaft, an elongated sheath surrounding a longitudinal portion of the shaft and slidable in longitudinal directions relative to the shaft, an energy storage element positioned on the longitudinal portion of the shaft, a retainer positioned at one end of the compartment, and a recess in the retainer. The valve may be loaded into the compartment with the retention member positioned in the recess and with the valve overlying at least a portion of the energy storage element.

The method may also include sliding the sheath in a first one of the longitudinal directions over the valve to radially compress the energy storage element and to hold the energy storage element in a compressed condition. The method may also include inserting the delivery device in a patient to position the valve at a target location and sliding the sheath in a second one of the longitudinal directions to uncover the valve. The energy storage element may be released from the compressed condition and may radially expand to impart an outward radial force to the valve. The energy storage element may be an elastomeric element surrounding at least a part of the longitudinal portion of the shaft. The energy storage element may include a leaf spring attached to the shaft. The energy storage element may be a recess insert, the recess insert overlying a bottom surface of the recess.

Another delivery device for an implantable medical device having a retention member at an end thereof may include a shaft extending in a longitudinal direction and defining a longitudinal axis, an elongated sheath surrounding a longitudinal portion of the shaft, a compartment defined inside the sheath and adapted to receive the medical device in an assembled condition, a retainer positioned at one end of the compartment, and a balloon extending along at least part of the longitudinal portion of the shaft. The sheath may be slidable relative to the shaft in the longitudinal direction.

The retainer may include a recess adapted to receive the retention member of the medical device in the assembled condition. The recess may have a bottom surface located a first distance from the longitudinal axis. The balloon may have a deflated state in which an outer surface of the balloon is located a second distance from the longitudinal axis, the second distance being less than the first distance. The balloon may have an inflated state in which the outer surface of the balloon is located a third distance from the longitudinal axis, the third distance being greater than the first distance.

Yet another delivery device for an implantable medical device having a retention member at an end thereof may include a shaft extending in a longitudinal direction and defining a longitudinal axis, an elongated sheath surrounding a longitudinal portion of the shaft, a compartment defined inside the sheath and adapted to receive the medical device in an assembled condition, and a retainer positioned at one end of the compartment. The retention member may have an angled lateral edge. The sheath may be slidable relative to the shaft in the longitudinal direction.

The retainer may include a recess adapted to receive the retention member of the medical device in the assembled condition. The retainer may have a retention edge facing the compartment. The recess may have a first region sized to receive the retention member. The recess may include a protuberance defining both a narrowed neck between the first region and the retention edge and an angled sidewall of the first region. In the assembled condition, an angle formed between the angled sidewall and the longitudinal axis may be greater than an angle formed between the angled lateral edge and the longitudinal axis.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a surgeon using the disclosed delivery devices. "Proximal" is to be understood as relatively close to the surgeon and "distal" is to be understood as relatively farther away from the surgeon.

Figure 1A:
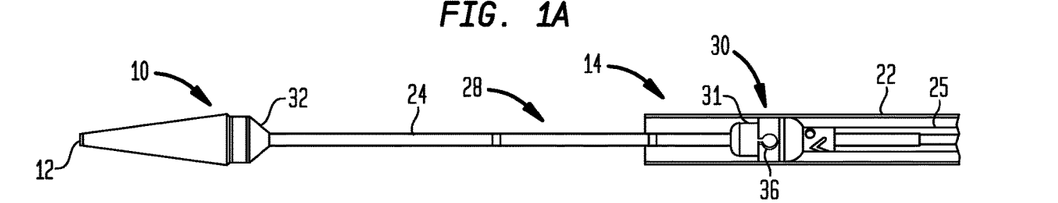
FIG. 1A is a side view of a transfemoral delivery device for a collapsible prosthetic heart valve.
Figure 1B:
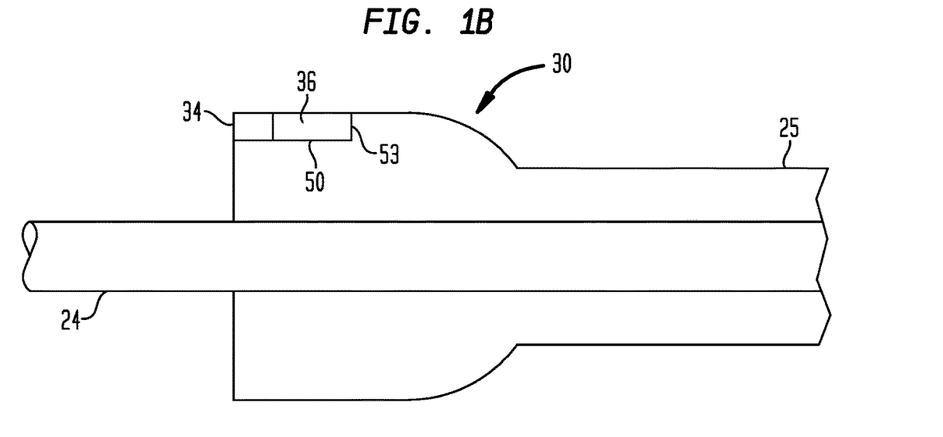
FIG. 1B is a longitudinal cross-section of a retainer of a delivery device depicted in FIG. 1A, shown without the proximal conical end or the distal sheath.
Figure 1C:
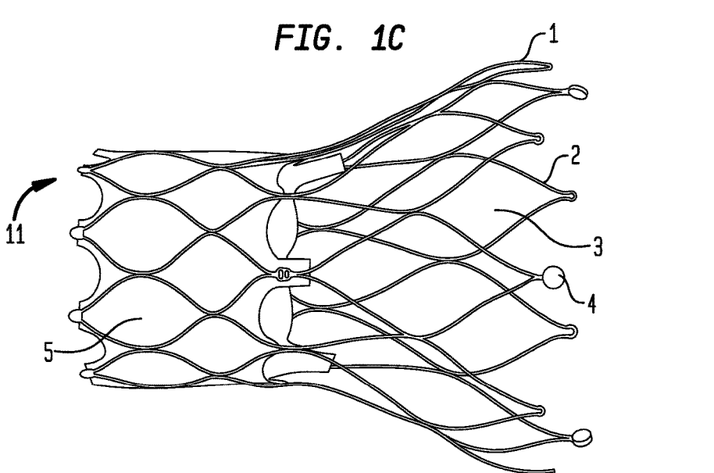
FIG. 1C is one embodiment of a collapsible prosthetic heart valve that can be delivered with the device of FIG. 1A.

Referring now to FIGS. 1A, 1B, and 1C to illustrate the structure and function of the present invention, a first embodiment of a delivery device 10 has a distal tip 12 and a catheter assembly 14 extending from the distal tip to a proximal end (not shown) that includes a handle (not shown) for a user to control the delivery device 10. The delivery device 10 is an exemplary transfemoral delivery device for a collapsible prosthetic heart valve. Examples of handles that can be used to control deployment of the delivery device 10 are shown and described in U.S. Patent Application Publication No. 2012/0123528, which is hereby incorporated by reference herein.

The catheter assembly 14 includes a distal sheath 22 extending from the handle towards the distal tip 12, a hollow inner shaft 24 located inside of the distal sheath and extending from the handle to the distal tip, and a valve receiving compartment 28 configured to receive a collapsible prosthetic heart valve or other implantable device, such as the valve 11 shown in FIG. 1C, for delivery inside of a patient. The valve 11 may have a stent portion 1 that includes a plurality of stent struts 2 that define cells 3 therebetween. At least one retention member 4 may extend from an end of the stent portion 1. The valve 11 may also have a valve portion 5 stitched or otherwise attached to the stent portion 1.

The valve receiving compartment 28 includes a retainer 30 located, in this embodiment, inside the distal sheath 22, a proximal conical end 31 adjacent the retainer 30, and a distal conical end 32 spaced from the retainer 30. The conical end 32 is joined to the inner shaft 24 at one end of the valve receiving compartment 28, and the conical end 31 and the retainer 30 are joined to a stiffening member 25 mounted on the inner shaft 24 at the other end of the valve receiving compartment 28. Preferably, the inner shaft 24 and the stiffening member 25 have the same internal diameter, adapted to receive a guide wire (not shown). Alternatively, in any of the delivery device embodiments described herein, the inner shaft 24 and the stiffening member 25 may be a single unitary shaft.

The retainer 30 may define one or more recesses 36, each recess being located at or adjacent the retention edge 34 of the retainer and configured to receive a corresponding retention member 4 of the stent portion 1 of the collapsible valve 11. For delivery into a patient, the collapsible valve 11 is loaded into the valve receiving compartment 28 around the inner shaft 24 and between conical ends 31 and 32, and the stent portion 1 of the valve is coupled to the retainer 30 while placing at least one retention member 4 into at least one recess 36.

Regardless of whether a valve 11 is to be delivered transfemorally into a patient to replace a native valve (e.g., the patient's aortic valve, mitral valve, etc.) using a device such as the device 10 shown in FIG. 1A, or transapically using a device such as the device 10' described below with respect to FIG. 2, the stent portion 1 of the valve 11 preferably is attached to the retainer 30, 30' by the retention members 4 protruding from the end of the stent that is opposite the end at which the valve is located (i.e., the retention members protrude from the aortic side of the stent). Preferably, the retention members 4 are positioned at the end of the valve 11 that is to be deployed last, i.e., the end of the valve that will be covered by the distal sheath the longest.

For example, in a transfemoral prosthetic aortic valve delivery device (e.g., the device 10 shown in FIG. 1A), the retention edge 34 of the retainer 30 is located at the distal end thereof, and the sheath 22 is moved in a proximal direction to unsheathe and deploy the valve, with the distal end of the valve unsheathed first.

The retention edge 34 of the retainer 30 may have a chamfered outer edge, which may help reduce frictional forces acting between the sheath 22 and the retainer during unsheathing and resheathing of a stent. The retention edge of any of the retainer embodiments disclosed herein may have chamfered outer edges.

Each recess 36 may have a similar shape and a slightly larger size than the stent retention member 4 so as to capture same readily, but with only a small amount of relief therebetween. Forming recesses 36 with an appropriate shape and size may prevent longitudinal movement of the valve within the valve the receiving compartment 28, such as during deployment or resheathing procedures.

In other embodiments, the retainer 30 may be configured such that the recesses 36 are rotatable relative to the inner shaft 24, for example, as shown and described in United States Patent Application Publication No. 2012/0078350, which is hereby incorporated by reference herein.

To load the delivery device 10 with a collapsible prosthetic valve 11, a user attaches the stent portion 1 of the prosthetic valve into the compartment 28 and to the retainer 30, compressing or crimping the valve until it fits inside the distal sheath 22, which holds the valve in a compressed state until the user decides to deploy the valve. When the valve 11 is later deployed by unsheathing, the stent portion 1 self-expands and is ultimately disengaged from the delivery device 10 once the retention members 4 are released from the retainer 30. If the valve 11 has not been fully deployed, i.e., if a portion of the valve remains in a collapsed state beneath the distal sheath 22, the valve may be resheathed by sliding the distal sheath back over the portion of the stent that has expanded, thereby recollapsing the expanded portion of the stent.

Figure 2:
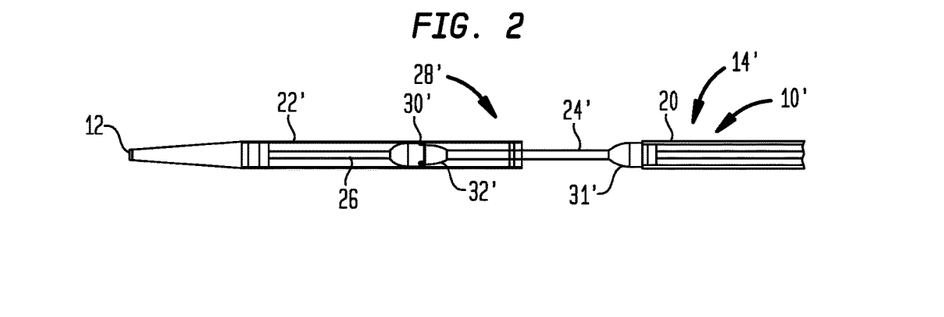
FIG. 2 is a side view of a transapical delivery device for a collapsible prosthetic heart valve.

Referring to FIG. 2, a second embodiment of a delivery device 10' has a distal tip 12 and a catheter assembly 14' extending from the distal tip to a proximal end (not shown) that may include a handle (not shown) for a user to control the delivery device 10'. The delivery device 10' is an exemplary transapical delivery device for a collapsible prosthetic heart valve.

The catheter assembly 14' may include a proximal sheath 20 extending from the handle towards the distal tip 12, a distal sheath 22' extending from the distal tip 12 towards the handle, a hollow tube 26 that extends slidably from the proximal end through the proximal sheath 20 and attaches to the distal sheath 22' at the distal tip 12 of the delivery device 10', and a valve receiving compartment 28' configured to receive a collapsible prosthetic valve, such as the valve 11 shown in FIG. 1C, for delivery inside of a patient.

The valve receiving compartment 28' is configured to receive a collapsible prosthetic heart valve such as the valve 11. The valve receiving compartment 28' includes a proximal conical end 31' at the distal end of the proximal sheath 20, a distal conical end 32' spaced from the proximal conical end, and a retainer 30' located, in this embodiment, adjacent the distal conical end 32' and inside the distal sheath 22'. A hollow inner shaft 24' is connected at one end to the proximal conical end 31' and at the other end to the distal conical end 32', and slidably receives the hollow tube 26 therethrough. For delivery into a patient, a collapsible valve 11 is loaded into the valve receiving compartment 28' around the inner shaft 24' and between the conical ends 31' and 32', and the stent portion of the valve is coupled to the retainer 30'.

The retainer 30' may be the same as the retainer 30 shown and described above, but with a sufficient central bore extending longitudinally therethrough to permit the hollow tube 26 to be slidably received therethrough.

As can be seen in FIG. 2, in a transapical prosthetic aortic valve delivery device such as the device 10', the retention edge 34 is located at the proximal end of the retainer 30', and the distal sheath 22' is moved in a distal direction to unsheathe and deploy the valve, with the proximal end of the valve unsheathed first.

The retainers, elastomeric elements, and/or springs described below can be used in either the transfemoral or the transapical delivery devices 10 and 10' described above with respect to FIGS. 1A, 1B, and 2. Also, the inventive retainers, elastomeric elements, and springs shown and described in this application may be configured to be used with other types of tube-like delivery devices for collapsible implantable devices. However, for convenience, the retainers, elastomeric elements, and springs will be described with respect to the transfemoral device 10. In this aspect of the invention, the delivery device is provided with at least one member (e.g., an elastomeric element or spring) uniquely suited to assist in the rapid and smooth ejection of the implantable device from the delivery device when desired. This member can provide a force against at least one portion of the stent, urging that portion to disengage from the delivery device.

Referring to FIGS. 3A-3D, the device 10 may include an elastomeric element 40 disposed or situated over at least a portion of the inner shaft 24 and optionally attached to a distal portion of the retainer 30. When the heart valve 11 is assembled or fitted to the retainer 30 such that the retention members 4 are engaged with the recesses 36 and the distal sheath 22 is covering the compartment 28 containing the valve, the elastomeric element 40 is adapted to be under radial compression from the stent and sheath, such that when the distal sheath is removed from the compartment, the stored energy within the elastomeric insert pushes radially outwardly against the stent, thereby assisting the removal of the retention members from the corresponding recesses 36 and assisting in the separation of the valve from the delivery device 10.

The elastomeric element 40 may include a proximal portion 41 adjacent the retention edge 34 of the retainer 30 and a distal portion 42 that extends from the proximal portion at least a portion of the distance towards the distal end of the compartment 28. As shown in FIGS. 3A-3D, the diameter of the elastomeric element 40 may taper from a first diameter D1 at the proximal portion 41 to a second diameter D2 at the distal portion 42. One or more of the proximal portion 41 and the distal portion 42 may also taper within the respective portion. For example, the distal portion 42 may taper from a wider diameter adjacent the proximal portion 41 to a smaller diameter remote from the proximal portion. In other embodiments (not shown), the proximal portion 41 and the distal portion 42 may have the same diameter, or the distal portion may have a greater diameter than the proximal portion.

Figure 3A:
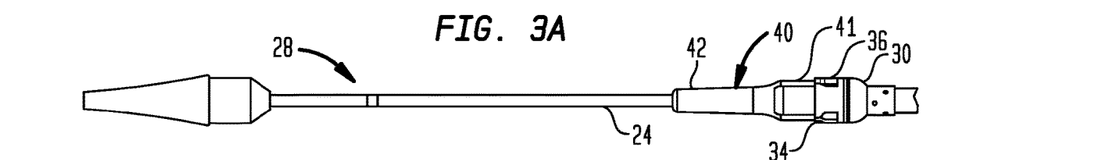
FIG. 3A is a side view of a transfemoral delivery device including an elastomeric element.
Figure 3B:
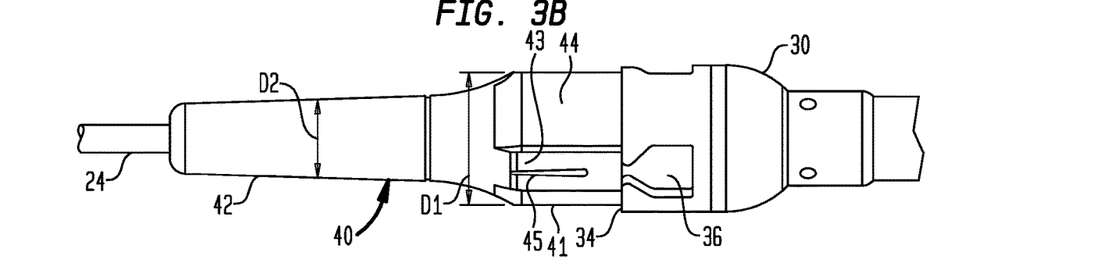
FIG. 3B is an enlarged side view of a portion of the device of FIG. 3A.
Figure 3C:
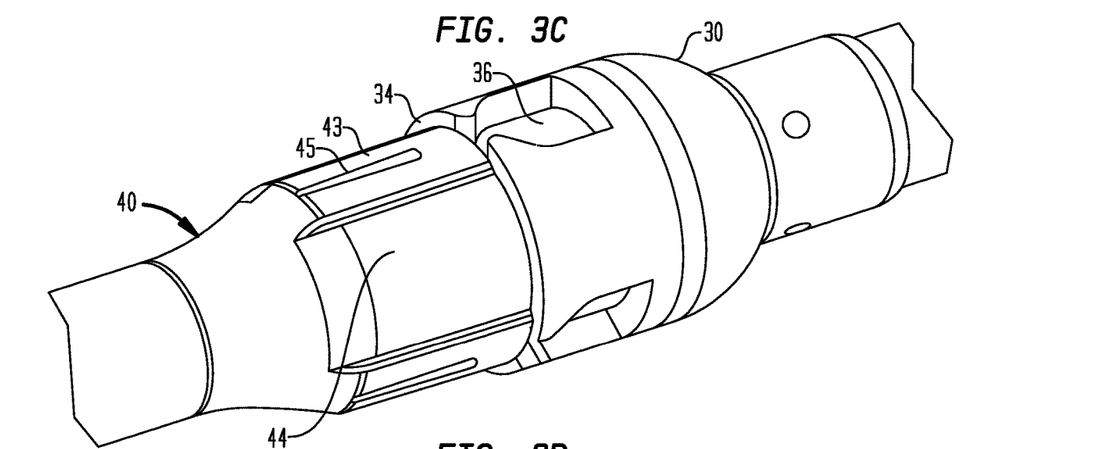
FIG. 3C is an enlarged perspective view of a portion of the device of FIG. 3A.
Figure 3D:
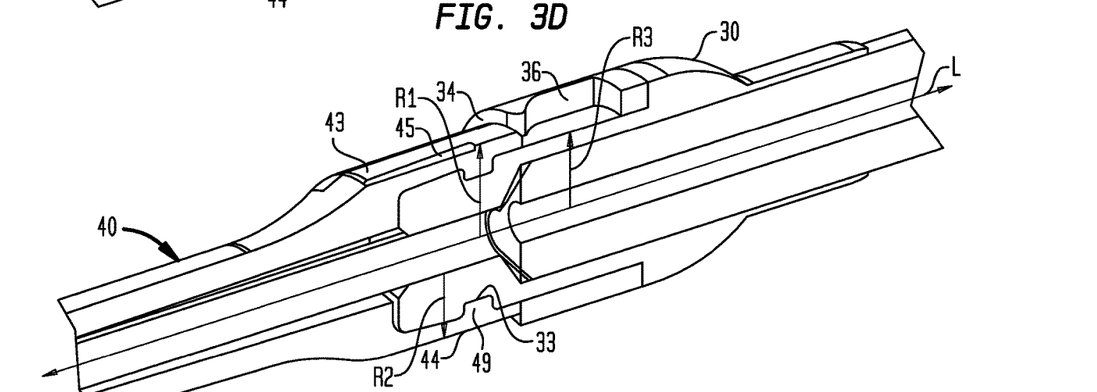
FIG. 3D is a longitudinal cross-section of the device of FIG. 3C.

The elastomeric element 40 may have a plurality of raised portions 43 and lowered portions 44, the raised and lowered portions alternating around the circumference of the elastomeric element such that the raised portions are oriented at the same circumferential locations as the recesses 36. The raised portions 43 may extend a first radial distance R1 from the longitudinal axis L of the retainer 30, and the lowered portions 44 may extend a second radial distance R2 from the longitudinal axis L, the first radial distance being greater than the second radial distance. The bottom surface 50 of the recess 36 may be located a third radial distance R3 from the longitudinal axis L of the retainer 30, the third radial distance being less than the first radial distance. In some embodiments, as shown in FIGS. 3D, the third radial distance R3 may be less than both the first and second radial distances R1 and R2.

By having the raised portions 43 that are circumferentially aligned with the recesses 36 extend to a greater radial distance from the longitudinal axis L than the bottom surface 50, the proximal portion 41 of the elastomeric element 40 will be partially radially compressed at least at the locations of the raised portions, thereby storing energy, when the retention elements 4 are pushed against the bottom surface 50 of the recess when the distal sheath 22 is covering the elastomeric element, the valve 11, and the retainer 30.

By having the lowered portions 44 extend to a lesser radial distance from the longitudinal axis L than the raised portions 43, the width in a radial direction of the retention edge 34 of the retainer 30 will be greater at locations circumferentially separated from the recesses 36 than the width of the retention edge at or adjacent the recesses. Since the stent struts 2 that do not have retention members 4 may abut the retention edge 34 when the valve 11 is loaded into the device 10, such a configuration having lowered portions 44 may permit easier loading of the valve into the device, because the stent struts that do not have retention members will have a greater surface of the retention edge to contact during the loading process, reducing the chance that such stent struts will slip off the retention edge during loading of the valve.

It is not required that the proximal portion 41 have raised portions and lowered portions; the proximal portion may have a surface located at a single radial distance around the circumference of the elastomeric element. However, it is preferred that such a single radial distance be greater than the third radial distance R3 at which the bottom surface 50 of the recess 36 is located, so that the proximal portion 41 of the elastomeric element 40 will be partially radially compressed when the distal sheath 22 pushes the retention elements 4 against the bottom surface 50 of the recess 36.

The elastomeric element 40 may also have an optional alignment feature in the form of a slot 45 within each of the raised portions 43 that is aligned with the center of the corresponding recess 36. As shown in FIGS. 3A-3D, the alignment feature is in the form of a slot 45 that is recessed below the surface of the corresponding raised portion 43. However, the alignment feature may alternatively be in the form of a raised rib that is adapted to fit into a cell 3 between adjacent stent struts 2, or it may be in the form of a marking or indicia that is neither raised nor lowered with respect to the surface of the raised portion 43. The alignment feature, regardless of whether it is a slit, a rib, or a surface marking or indicia, may also be in an indicative shape such as a letter, number, arrow, or the like.

The retainer 30 may include a circumferential groove 33 (FIG. 3D) adjacent the retention edge 34 that is adapted to receive a corresponding circumferential rib 49 of the elastomeric element 40 during assembly of the elastomeric insert to the retainer 30. As shown in FIG. 3D, the circumferential rib 49 is located in the proximal portion 41 of the elastomeric element 40, but that need not be the case. In other embodiments (not shown), the elastomeric element 40 may include a circumferential rib in the distal portion 42 thereof, and the circumferential rib may be adapted to be received in a corresponding circumferential groove in the inner shaft 24. In other embodiments, other conventional interlocking mechanisms may be used to couple the elastomeric element 40 to the inner shaft 24 and/or the retainer 30, such as a plurality of grooves disposed on a tapered distal portion of the retainer interlocking with a plurality of ribs located in a tapered inner lumen of the elastomeric element. The elastomeric element 40 may also be glued or affixed to the inner shaft 24 and/or the retainer 30 in any conventional manner.

Figure 3E:
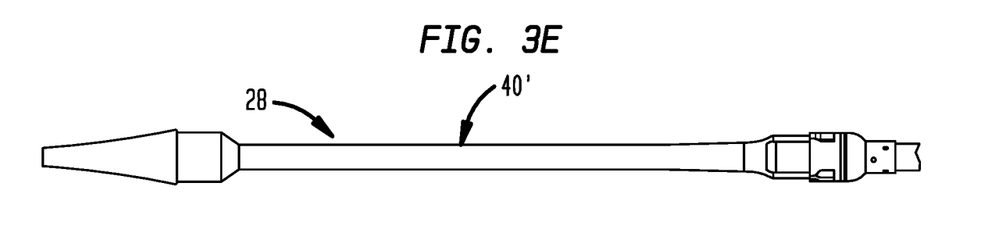
FIG. 3E is a side view of a transfemoral delivery device including an alternative elastomeric element running along a relatively greater length of the component.

It is contemplated that multiple variants of the elastomeric element 40 may be provided. For example, as shown in FIG. 3E, the elastomeric element 40' may extend the entire length of the compartment 28 to assist in the radial expansion and/or release of the entire valve. In other embodiments, a plurality of smaller elements of varying diameter and composition may be used at different locations within the compartment. The amount of force that can be exerted will depend upon, for example, the elastomeric material used, its density and elasticity, its thickness and dimensions, and the degree that it is compressed by the valve 11 once the distal sheath 24 is slid over the compartment 28. Suitable materials for the elastomeric element 40 include, for example, silicone, urethane, nylon, pebax, santoprene, butyl, neoprene, or a combination thereof. In one example, a plurality of spaced-apart energy storage elements made of an elastomer or another energy storage material may be distributed about the inner shaft 24 in a circumferential direction perpendicular to the longitudinal direction L (e.g., in the configuration shown in FIG. 7D).

Alternatively, or in combination with the elastomeric element 40 or 40', one or more of the recesses 36 may include an elastomeric material therein to assist in ejecting the retention members therefrom.

Figure 4A:
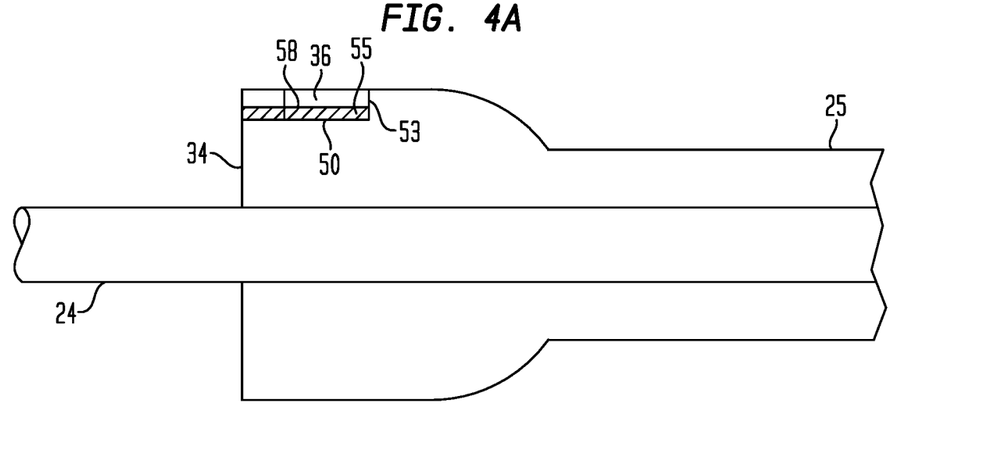
FIG. 4A is a side view of another embodiment of a retainer suitable for use in the delivery device of FIGS. 1A and 2.

For example, as shown in FIG. 4A, one or more of the recesses 36 may each define a bottom surface 50, and a pad or section of an elastomeric material, as described above for the elastomeric element 40, in the form of an elastomeric insert 55 may be deposited into the recess overlying the bottom surface. The elastomeric insert 55 may be attached to the bottom surface 50 in numerous ways, including, for example, an adhesive material. In a particular example, all of the recesses 36 may include an elastomeric insert 55 therein.

The elastomeric insert 55 can have a planar upper surface 58 that has a contour that conforms to the contour of the bottom surface 50 of the recess 36, or alternatively, the elastomeric insert may have an upper surface that has a contour that does not conform to the contour of the bottom surface of the recess. In one example of an upper surface 58 that is conformal to the bottom surface 50, the upper surface may be convexly curved in a direction around the longitudinal axis of the inner shaft 24, such that the upper surface of each of the elastomeric inserts forms a portion of a cylinder.

Figure 4B:
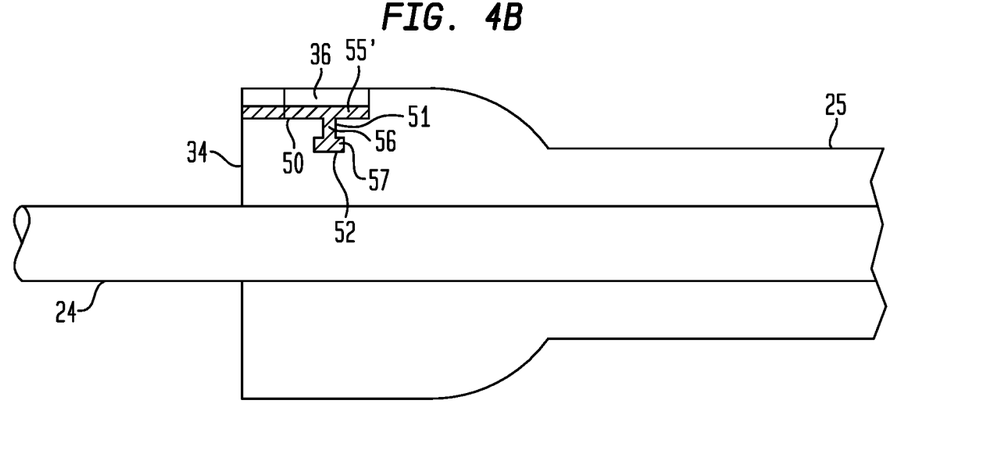
FIG. 4B is a side view of another embodiment of a retainer suitable for use in the delivery device of FIGS. 1A and 2.

As shown in FIG. 4B, in an alternative embodiment of the elastomeric insert 55 shown in FIG. 4A, an elastomeric insert 55' may be attached to the bottom surface 50 by interlocking of a prong 56 into a recess 51 extending into the retainer 30 from the bottom surface of the recess 36. The prong 56 can have one or more tabs 57 that extend from the prong in a direction that is transverse to the longitudinal axis of the prong, and the tabs can be adapted to fit into corresponding notches 52 extending in a direction that is transverse to the longitudinal axis of the recess 51.

In another alternative embodiment of the elastomeric insert 55 shown in FIG. 4A, one or more of the recesses 36 may each be partially or completely lined with an elastomeric layer that may be conformally or non-conformally deposited within the recess. Such an elastomeric layer may extend only across the bottom surface 50 of the recess, or it may extend across the bottom surface and sidewalls 53 of the recess that extend from the bottom surface in a direction that is transverse to a plane of the bottom surface.

Still further, the retainer 30 may itself be formed from an elastomeric material so as to slightly compress when covered by the distal sheath 22, but then radially expand when exposed, thereby facilitating the release of the retention members therefrom.

Alternatively, or in combination with the elastomeric element 40 or 40', the device 10 may include a balloon to assist in ejecting the retention members therefrom. Rather than using an elastomeric material, the elastomeric elements 40 and 40' and all variants thereof (e.g., the elastomeric inserts 55, 55' of FIGS. 4A and 4B) may be fashioned from a balloon that will exert an outward radial force when no longer constrained by the distal sheath 22 and inflated, and thereby help eject the retention members from the recesses 36.

Figure 5A:
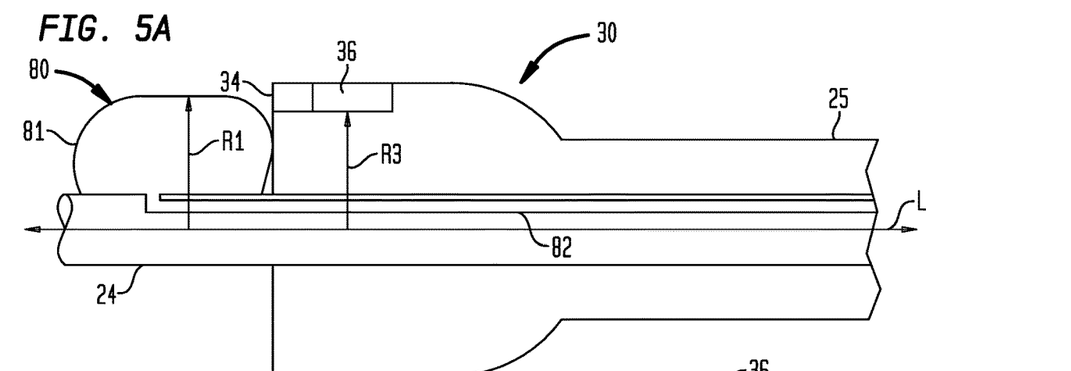
FIG. 5A is a side view of a portion of a transfemoral delivery device including a balloon.
Figure 5B:
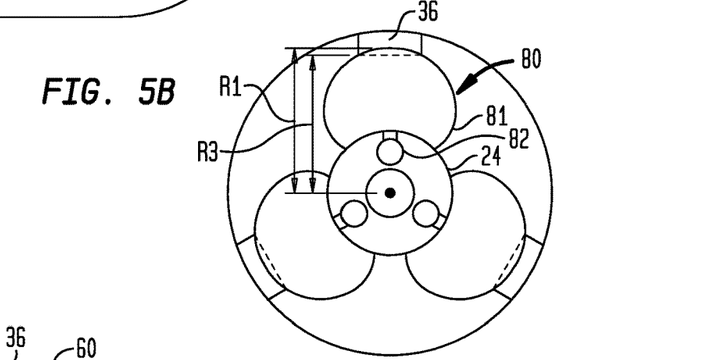
FIG. 5B is an end view of a portion of the device of FIG. 5A.

For example, as shown in FIGS. 5A and 5B, the insert 40 can be replaced with a balloon assembly 80 having a plurality of lobes 81 attached to and extending around the inner shaft 24 for a portion of or the entire length of the compartment 28. Each of the lobes 81 may be in fluid communication with one or more inflation lumens 82 each extending between a proximal end of the device 10 (not shown) and one or more of the lobes. As shown in FIG. 5B, each of the lobes 81 may be supplied with fluid by a corresponding inflation lumen 82. Alternatively, a single inflation lumen may be in fluid communication with all of the lobes 81, or a plurality of inflation lumens may be in fluid communication with each of the lobes.

As shown in FIG. 5B, the balloon assembly 80 may have three lobes 81, each lobe circumferentially aligned with a corresponding one of the recesses 36. Alternatively, the balloon assembly 80 may have a single lobe extending around a portion of or all of the circumference of the inner shaft 24, or the balloon assembly may have any other number of lobes, including for example, one, two, four, six, eight, or nine. However, it is preferred that the number of lobes be equal to the number of recesses.

Similar to the raised portions 43 of the elastomeric element 40 described above, the lobes 81 of the balloon assembly 80, when inflated, may each extend a first radial distance R1 from the longitudinal axis L of the retainer 30, and the bottom surface 50 of the recess 36 may be located a third radial distance R3 from the longitudinal axis L of the retainer 30, the third radial distance being less than the first radial distance.

By having the lobes 81 that are circumferentially aligned with the recesses 36 extend to a greater radial distance from the longitudinal axis L than the bottom surface 50, the lobes can be inflated to a sufficient radius to contact the stent struts 2 having retention elements 4, thereby facilitating the release of the retention members from the recesses 36.

The valve 11 may be loaded into the device 10 when the lobes 81 are deflated (i.e., without a substantial amount of fluid therein), so that the space within the compartment 28 occupied by the lobes may be minimized during insertion of the distal portion of the device into a patient.

When the distal sheath 22 is moved to uncover the compartment 28, a fluid (e.g., a liquid such as saline, a gas such as air, etc.) may be selectively flowed into lobes 81 by the user to inflate the lobes. Each of the lobes 81, when inflated, may exert an outward radial force against the stent portion 1 of the valve 11, or, more specifically, against the stent struts 2 having retention members 4 attached thereto, so that the lobes may contact and push the stent radially outward, thereby facilitating the release of the retention members 4 from the recesses 36.

Although not shown in the figures, aspects of the elastomeric element and balloon-based embodiments may be combined into a single embodiment. For example, portions of the elastomeric element 40, e.g., the raised portions 43, may be replaced by balloon lobes that can be selectively inflated to facilitate the release of the retention members 4 from the recesses 36.

Rather than using an elastomeric material or a balloon, the elastomeric elements 40 and 40', the balloon assembly 80, and all variants thereof (e.g., the elastomeric inserts 55, 55' of FIGS. 4A and 4B) may be fashioned from a compression spring, spring steel, shape memory material, and the like that will exert an outward radial force when no longer constrained by the distal sheath 22, and thereby help eject the retention members from the recesses 36.

Figure 6A:
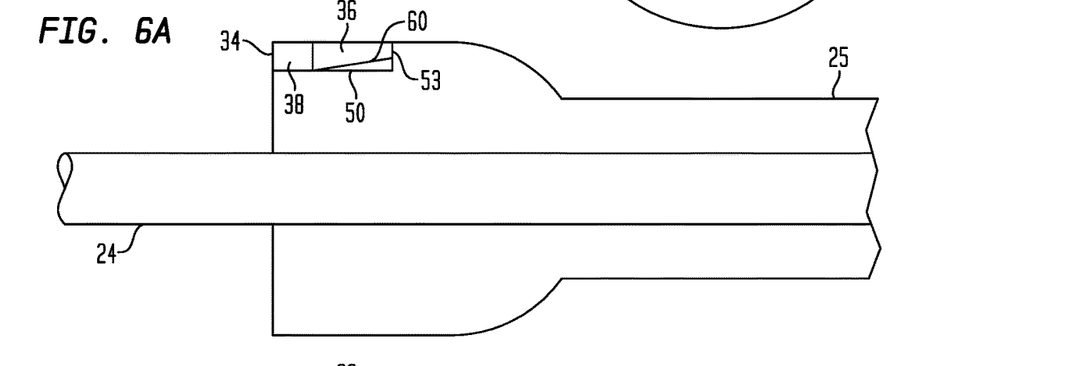
FIG. 6A is a side view of another embodiment of a retainer suitable for use in the delivery device of FIGS. 1A and 2.
Figure 6B:
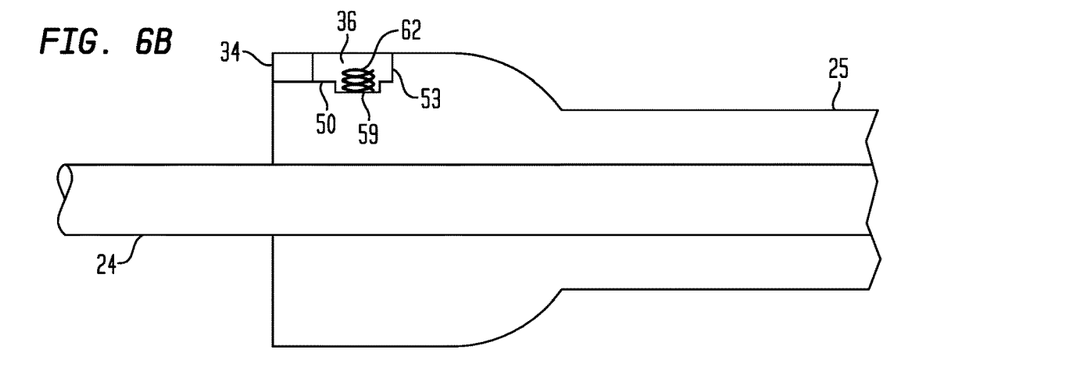
FIG. 6B is a side view of another embodiment of a retainer suitable for use in the delivery device of FIGS. 1A and 2.

For example, as shown in FIGS. 6A and 6B, one or more of the recesses 36 may include a spring in the form of a leaf spring 60 (FIG. 6A), a coil spring 62 (FIG. 6B), or any other conventional configuration therein that is biased to exert an outward radial force when a retention member 4 is pushed radially inward against it by the distal sheath 22 when the distal sheath is covering the compartment 28. When the distal sheath 22 is moved to uncover the compartment 28, the stored energy in the spring 60 or 62 may be released, and the spring may push the retention member radially outward, thereby facilitating the release of the retention members from the recesses 36.

The leaf spring 60 shown in FIG. 6A may be attached to the bottom surface 50 or one of the sidewalls 53 of the recess 36. As shown, the leaf spring 60 is attached to a portion of the bottom surface 50 adjacent the narrowed neck portion 38. The coil spring 62 shown in FIG. 6B may be attached to the bottom surface 50, one of the sidewalls 53, or a recess 59 extending below the bottom surface of the recess 36. As shown, the coil spring 62 is attached to a surface of a recess 59 extending below the bottom surface 50 of the recess 36.

In other examples, as shown in FIGS. 7A-7D, the insert 40 can be replaced with a spring in the form of a single coiled leaf spring 70 attached to and extending around the inner shaft 24 (FIGS. 7A and 7B), a plurality of curved leaf springs 71 each attached to and extending partially around the inner shaft 24 (FIG. 7C), or one or more straight or curved leaf springs 72 attached to the inner shaft and extending in the longitudinal direction of the inner shaft (FIG. 7D) for part or the entire length of the compartment 28.

Each of the leaf springs 70, 71, and 72 may be biased to exert an outward radial force when the stent portion 1 of the valve 11 is pushed radially inward against it by the distal sheath 22 when the distal sheath is covering the compartment 28. When the distal sheath 22 is moved to uncover the compartment 28, the stored energy in the springs 70 or 72 may be released, and the springs may push the stent radially outward, thereby facilitating the release of the retention members 4 form the recesses 36.

Figure 7A:
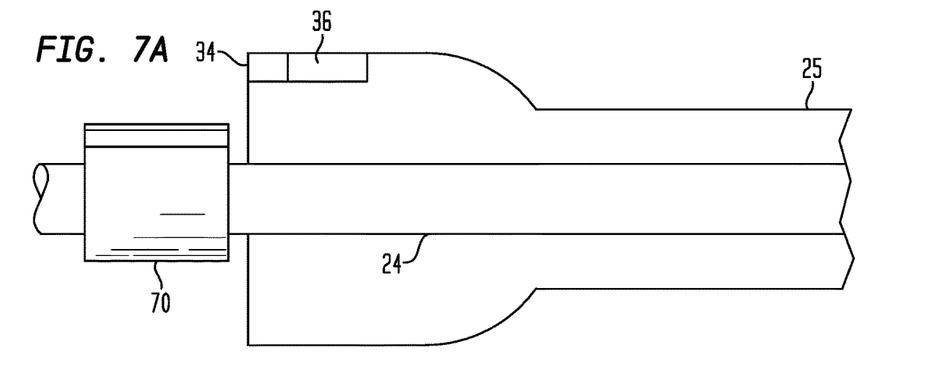
FIG. 7A is a side view of a transfemoral delivery device including a coiled spring attached to the inner shaft.
Figure 7B:
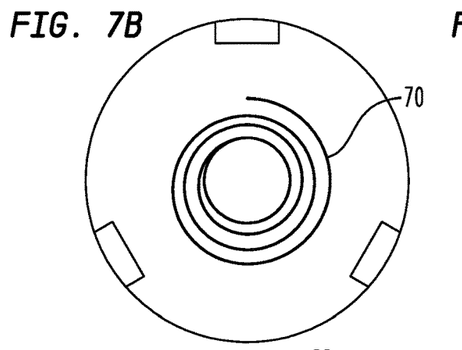
FIG. 7B is an end view of a portion of the device of FIG. 7A.
Figure 7C:
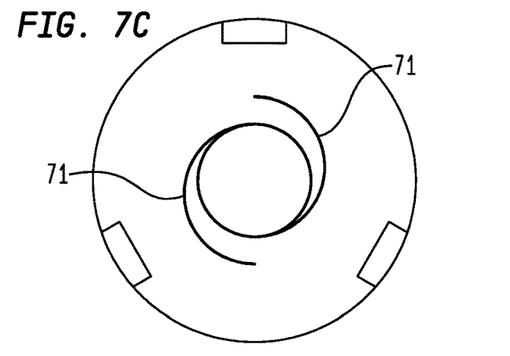
FIG. 7C is an end view of a device that is a variation of the device of FIG. 7A.

The coiled leaf spring 70 shown in FIGS. 7A and 7B may be attached to the inner shaft 24 and may extend around the inner shaft for any portion of the circumference of the inner shaft. For example, as shown, a single coiled leaf spring 70 extends 1080° (three times) around the inner shaft 24. In other embodiments, a coiled leaf spring can extend any number of times around the inner shaft 24, including once or twice. Alternatively, as shown in FIG. 7C, a plurality of curved leaf springs 71 can extend around a portion of the circumference of the inner shaft 24, such as two leaf springs each extending around 180° (half) of the circumference of the inner shaft 24.

Figure 7D:
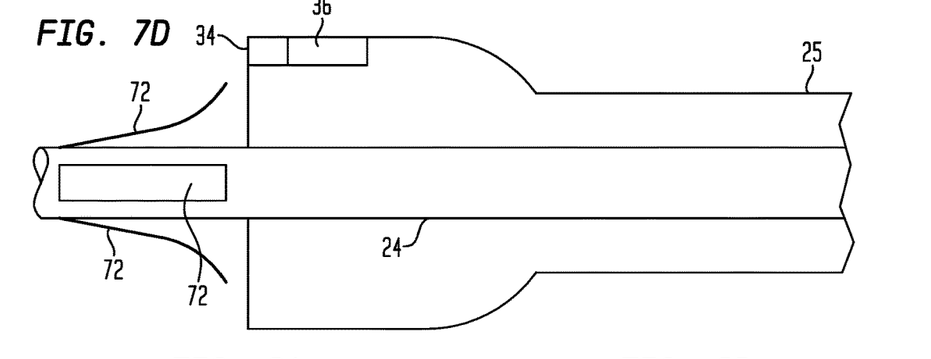
FIG. 7D is a side view of a transfemoral delivery device including leaf springs attached to the inner shaft.

As shown in FIG. 7D, or one or more straight or curved leaf springs 72 may attached to the inner shaft 24 and may extend in the longitudinal direction of the inner shaft for part or the entire length of the compartment 28. There may be a plurality of springs 72 attached to the inner shaft at a plurality of respective circumferential locations around the inner shaft 24, such that each spring is circumferentially aligned with a corresponding one of the recesses 36. However, in other embodiments, there may be more or less springs 72 than recesses. In one example, there may be six circumferentially spaced springs 72 and three recesses 36, so that every other spring is circumferentially aligned with a corresponding recess, and the remaining springs are located between adjacent ones of the recesses. Similar to raised portions 43 and the lobes 81 described above, the springs 72 that are circumferentially aligned with the recesses 36 may be biased to extend to a greater radial distance from the longitudinal axis of the retainer 30 than the bottom surface 50, so that when the distal sheath 22 is withdrawn from the valve, the springs may contact the stent struts 2 having retention elements 4, thereby facilitating the release of the retention members from the recesses 36.

It is to be understood that many of the energy storage elements described herein, such as the elastomeric materials extending around the inner shaft 24 and extending within the recesses 36, and the springs extending around the inner shaft and extending within the recesses, can be combined with one another in a single device. For example, the elastomeric element 40 can extend around the inner shaft 24, while the leaf springs 60 can be disposed in corresponding ones of the recesses 36. Any combination of the embodiments described above can be used in a single device.

As the delivery devices described herein are advanced into a patient, such as through the femoral artery towards the aorta, the stent portion 1 of the prosthetic valve 11 may become twisted about its longitudinal axis relative to the retainer due to the maneuvering of the delivery device through the vasculature, thereby applying torsional stress both to the stent and to the stent's retention members that are coupled to the recesses 36. Such torsional stress may increase friction between the retention members of the stent and the recesses 36, such that, when the distal sheath 22 uncovers the compartment 28 to deploy the valve, the force from the bias of the stent to radially expand may not be sufficient to free all of the retention members from the recesses. The ability of the energy storage elements described herein to store energy may allow the retainer provide a radially-outward force when the distal sheath 22 uncovers the valve in the compartment 28, thereby aiding release of the valve from the compartment by helping to overcome friction between the retention members of the stent and the recesses. It will be appreciated that the various springs described herein can be made of any conventional material, including metal, memory metal, plastic, and the like.

Figure 8A:
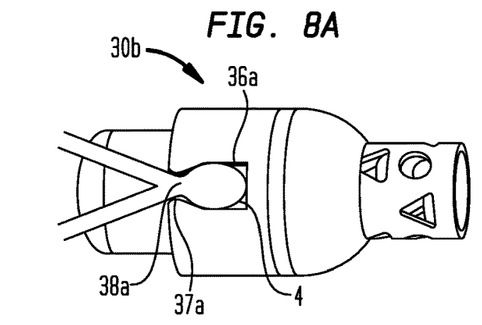
FIG. 8A is a side perspective view of an alternative embodiment of a valve retainer.
Figure 8B:
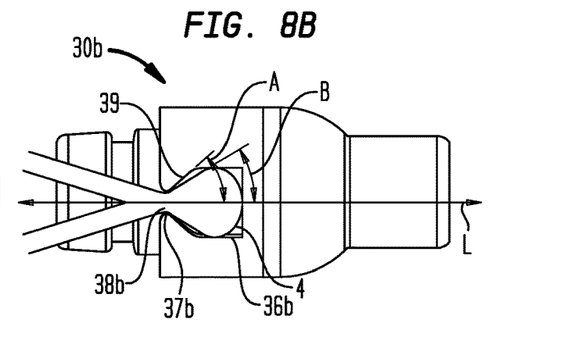
FIG. 8B is a side view of another embodiment of a valve retainer.

FIGS. 8A and 8B show further alternate embodiments of the retainer 30 described above in connection with the embodiments of FIGS. 1A through 7D. The retainer embodiments shown in FIGS. 8A and 8B and described below may be used with any of the delivery devices described herein.

As shown in FIG. 8A, the retainer 30a has recesses 36a with protuberances 37a projecting towards one another to define a narrowed neck 38a that limits the longitudinal movement of a corresponding retention member 4 of a heart valve stent toward a retention edge 34 of the retainer. The recesses 36a are configured to produce a surface contact between the retention member 4 and the protuberances 37a when a compressive, tensile, or torsional load is applied to the retention member.

As shown in FIG. 8B, the retainer 30b has recesses 36b with protuberances 37b projecting towards one another to define a narrowed neck 38b. The retention members 4 and the recesses 36b are preferably configured to produce as small of a surface contact as possible between the retention member 4 and an angled surface 39 or wall of the recess 36 when a compressive, tensile, or torsional load is applied to the retention member. Most preferred is a surface contact between the retention member 4 and an angled surface 39 of the recess that is close to a single point of contact between the retention member and the angled surface at either side of the recess, which is referred to herein as "point contact" between the two surfaces.

In one example, such a point contact may be achieved by having an angle A between the longitudinal axis L of the retainer 30 and an angled surface 39 of the recess that is greater than an angle B between the longitudinal axis of the recess and a corresponding portion of the retention member 4. In other examples, any combination of contours of the retention member 4 and the angled surface 39 of the recess 36 may be used that minimizes the contact surfaces between the angled surface and the retention member when a compressive, tensile, or torsional load is applied to the retention member.

Although three recesses 36 spaced 120° apart about the circumference of the retainer are shown FIGS. 7B and 7C, the device 10 (and all of the other retainers disclosed herein) may have any number of recesses, including for example, one, two, four, six, eight, or nine recesses. Further, each recess 36d (and all of the other recesses disclosed herein) may have only a single protuberance defining the neck, or any number of protuberances greater than two. Although three retention members 4 are described as being engaged in the three respective recesses 36 in the figures shown, the retainers described herein may be used with stents 1 having any number of retention members 4, including for example, one, two, four, six, or eight retention members.

Although the various retainer embodiments have been described here in connection with retaining for deployment a prosthetic valve having a collapsible stent structure, all of the retainer embodiments may be used for other purposes. In particular, the various embodiments of retainers may be used to retain conventional collapsible stents that do not contain a valve.

Although the invention herein has been described with reference to particular embodiments in which the annulus end of a prosthetic valve is deployed first, it is to be understood that the invention contemplates embodiments in which the aortic end of a valve is deployed first. In such embodiments (not shown), retention members may protrude from the annulus end of the stent portion of the valve for engagement with a retainer of the delivery device, such that the aortic end of the stent is remote from the retainer and may be unsheathed first. In still other embodiments (not shown), retention members may protrude from both the aortic and the annulus ends of the stent portion of the valve for engagement with a retainer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of deploying a prosthetic heart valve, the method comprising:
   positioning a retention member of the prosthetic heart valve, which is at an outflow end of the prosthetic heart valve, within a recess of a retainer of a delivery device;
   while the retention member is in the recess of the retainer, loading the prosthetic heart valve into the delivery device by sliding an outer sheath of the delivery device distally over the prosthetic heart valve to collapse the prosthetic heart valve into a compartment defined between the outer sheath and an inner shaft of the delivery device, so that an energy storage element is positioned between the prosthetic heart valve and the inner shaft;
   after loading the prosthetic heart valve into the delivery device, advancing the delivery device into the patient until the compartment is positioned adjacent to a native heart valve of the patient;
   with the compartment positioned adjacent to the native heart valve of the patient, beginning to withdraw the outer sheath proximally relative to the prosthetic heart valve to expose an inflow end of the prosthetic heart valve such that the inflow end of the prosthetic heart valve begins to self-expand away from the inner shaft while the outer sheath restricts the retention member from exiting the recess of the retainer;
   after allowing the inflow end of the prosthetic heart valve to begin to self-expand, further proximally withdrawing the outer sheath relative to the prosthetic heart valve until the outer sheath no longer restricts the retention member from exiting the recess of the retainer; and
   during the further proximal withdrawal of the outer sheath, the energy storage element imparts an outward radial force on the prosthetic heart valve to assist in ejecting the retention member from the recess of the retainer, the outward radial force being separate from self-expansion forces that cause the prosthetic heart valve to self-expand,
   wherein the energy storage element is a spring positioned within the recess of the retainer.

2. The method of claim 1, wherein the spring is a leaf spring.

3. The method of claim 2, wherein the leaf spring is attached to a bottom surface or one or more sidewalls of the recess of the retainer, and when the leaf spring imparts the outward radial force on the prosthetic heart valve, the outward radial force is imparted by the leaf spring directly on the retention member of the prosthetic heart valve.

4. The method of claim 1, wherein the spring is a coil spring.

5. The method of claim 4, wherein the coil spring is attached to a bottom surface of the recess of the retainer, one or more sidewalls of the recess of the retainer, or a surface of a cavity extending below the bottom surface of the recess of the retainer, and when the coil spring imparts the outward radial force on the prosthetic heart valve, the outward radial force is imparted by the coil spring directly on the retention member of the prosthetic heart valve.

6. A method of deploying a prosthetic heart valve, the method comprising:
   positioning a retention member of the prosthetic heart valve, which is at an outflow end of the prosthetic heart valve, within a recess of a retainer of a delivery device;
   while the retention member is in the recess of the retainer, loading the prosthetic heart valve into the delivery device by sliding an outer sheath of the delivery device distally over the prosthetic heart valve to collapse the prosthetic heart valve into a compartment defined between the outer sheath and an inner shaft of the delivery device, so that an energy storage element is positioned between the prosthetic heart valve and the inner shaft;

after loading the prosthetic heart valve into the delivery device, advancing the delivery device into the patient until the compartment is positioned adjacent to a native heart valve of the patient;

with the compartment positioned adjacent to the native heart valve of the patient, beginning to withdraw the outer sheath proximally relative to the prosthetic heart valve to expose an inflow end of the prosthetic heart valve such that the inflow end of the prosthetic heart valve begins to self-expand away from the inner shaft while the outer sheath restricts the retention member from exiting the recess of the retainer;

after allowing the inflow end of the prosthetic heart valve to begin to self-expand, further proximally withdrawing the outer sheath relative to the prosthetic heart valve until the outer sheath no longer restricts the retention member from exiting the recess of the retainer; and during the further proximal withdrawal of the outer sheath, the energy storage element imparts an outward radial force on the prosthetic heart valve to assist in ejecting the retention member from the recess of the retainer, the outward radial force being separate from self-expansion forces that cause the prosthetic heart valve to self-expand, wherein the retention member is coupled to a strut of the prosthetic heart valve, the retention member having a width in a circumferential direction of the prosthetic heart valve that is greater than a width of the strut in the circumferential direction of the prosthetic heart valve, wherein the energy storage element is an elastomeric element disposed immediately distally of the retainer, the elastomeric element having two lowered portions, and a raised portion aligned with the recess in a longitudinal direction of the inner shaft, the raised portion being positioned between the two lowered portions in a circumferential direction of the energy storage element wherein the raised portion extends a first radial distance from a central longitudinal axis of the retainer, the two lowered portions extend a second radial distance from the central longitudinal axis of the retainer, and a bottom surface of the recess extends a third radial distance from the central longitudinal axis of the retainer, the third radial distance being smaller than the first radial distance.

7. The method of claim 6, wherein when the energy storage element imparts the outward radial force on the prosthetic heart valve, the outward radial force is imparted directly on the strut.

8. The method of claim 6, wherein the third radial distance is smaller than the second radial distance.

9. A method of deploying a prosthetic heart valve, the method comprising:

positioning a retention member of the prosthetic heart valve, which is at an outflow end of the prosthetic heart valve, within a recess of a retainer of a delivery device;

while the retention member is in the recess of the retainer, loading the prosthetic heart valve into the delivery device by sliding an outer sheath of the delivery device distally over the prosthetic heart valve to collapse the prosthetic heart valve into a compartment defined between the outer sheath and an inner shaft of the delivery device, so that an energy storage element is positioned between the prosthetic heart valve and the inner shaft;

after loading the prosthetic heart valve into the delivery device, advancing the delivery device into the patient until the compartment is positioned adjacent to a native heart valve of the patient;

with the compartment positioned adjacent to the native heart valve of the patient, beginning to withdraw the outer sheath proximally relative to the prosthetic heart valve to expose an inflow end of the prosthetic heart valve such that the inflow end of the prosthetic heart valve begins to self-expand away from the inner shaft while the outer sheath restricts the retention member from exiting the recess of the retainer;

after allowing the inflow end of the prosthetic heart valve to begin to self-expand, further proximally withdrawing the outer sheath relative to the prosthetic heart valve until the outer sheath no longer restricts the retention member from exiting the recess of the retainer; and during the further proximal withdrawal of the outer sheath, the energy storage element imparts an outward radial force on the prosthetic heart valve to assist in ejecting the retention member from the recess of the retainer, the outward radial force being separate from self-expansion forces that cause the prosthetic heart valve to self-expand, wherein the energy storage element is a pad of compressible elastomeric material positioned within the recess of the retainer.

10. The method of claim 9, wherein the elastomeric material is selected from the group consisting of silicone, urethane, nylon, pebax, santoprene, butyl, neoprene, and combinations thereof.

11. The method of claim 9, wherein when the pad of compressible elastomeric material imparts the outward radial force on the prosthetic heart valve, the outward radial force is imparted by the pad of compressible elastomeric material directly on the retention member of the prosthetic heart valve.

12. The method of claim 9, wherein the pad of compressible elastomeric material is attached to a bottom surface of the recess by interlocking a prong on the pad of compressible elastomeric material into a cavity extending into the retainer from the bottom surface of the recess.

* * * * *